US007722813B2

United States Patent
Inoue et al.

(10) Patent No.: US 7,722,813 B2
(45) Date of Patent: May 25, 2010

(54) UREA CONCENTRATION IDENTIFICATION DEVICE FOR UREA SOLUTION

(75) Inventors: Shinichi Inoue, Ageo (JP); Akiko Kubota, Ageo (JP); Takayuki Takahata, Ageo (JP)

(73) Assignee: Mitsui Mining & Smelting Co., Ltd., Tokyo (JP)

( * ) Notice: Subject to any disclaimer, the term of this patent is extended or adjusted under 35 U.S.C. 154(b) by 1110 days.

(21) Appl. No.: 10/571,358

(22) PCT Filed: Sep. 10, 2004

(86) PCT No.: PCT/JP2004/013214

§ 371 (c)(1),
(2), (4) Date: Mar. 9, 2006

(87) PCT Pub. No.: WO2005/026710

PCT Pub. Date: Mar. 24, 2005

(65) Prior Publication Data

US 2007/0054409 A1    Mar. 8, 2007

(30) Foreign Application Priority Data

Sep. 11, 2003    (JP)    .............................. 2003-319776

(51) Int. Cl.
| G01N 15/06 | (2006.01) |
| G01N 27/30 | (2006.01) |
| C01B 21/00 | (2006.01) |
| G01N 27/00 | (2006.01) |

(52) U.S. Cl. .......................... 422/68.1; 422/55; 422/56; 422/57; 422/58; 422/82.01; 422/82.02; 422/82.04; 422/76; 204/177; 204/178; 204/431; 204/432; 204/433; 73/61.46; 374/45

(58) Field of Classification Search ....................... None
See application file for complete search history.

(56) References Cited

U.S. PATENT DOCUMENTS 6,214,206 B1    4/2001    Kriz ........................... 205/778
6,551,478 B1 *    4/2003    Bielawski et al. ........... 204/433

FOREIGN PATENT DOCUMENTS

| JP | 1-131155 | 6/1989 |
| JP | 1-304348 | 12/1989 |
| JP | 3-262949 | 11/1991 |
| JP | 11-153561 | 6/1999 |
| JP | 2001-20724 | 1/2001 |
| WO | 02/27280 A2 | 4/2002 |
| WO | 03/052372 | 6/2003 |

* cited by examiner

*Primary Examiner*—Jill Warden
*Assistant Examiner*—Neil Turk
(74) *Attorney, Agent, or Firm*—Frommer Lawrence & Haug LLP; Ronald R. Santucci

(57) ABSTRACT

A urea concentration identification device comprising a concentration identification sensor unit (2) and a support unit (4) attached at the bottom end thereof with this sensor unit and provided at the top end thereof with a mounting unit (4a) to a urea solution tank opening. The concentration identification sensor unit (2) has an indirectly-heated concentration detector and liquid temperature detector provided with metal fins (21c),(22c), respectively, for heat-exchanging with urea solution. The concentration identification sensor unit (2) is provided with a cover member (2d) that forms an opposite-ends-opened urea solution induction passage so as to surround the metal fins (21c), (22c). A single-pulse voltage is applied to the heating element of the indirectly-heated concentration detector to heat it, and a urea concentration is identified at an identification operation unit based on an output from a concentration detection circuit including the temperature sensing element of the indirectly-heated concentration detector and the liquid temperature detector.

5 Claims, 10 Drawing Sheets

UREA CONCENTRATION IDENTIFICATION DEVICE FOR UREA SOLUTION

This application is a 371 of PCT/JP2004/013214 filed on Sep. 10, 2004, published on Mar. 24, 2005 under publication number WO 2005/026710 A1 which claims priority benefits from Japanese Patent Application Number 2003-319776 filed Sep. 11, 2003.

TECHNICAL FIELD

The present invention relates to a device for identifying a urea concentration in urea solution which is to be sprayed to exhaust purification catalyst so as to decompose nitrogen oxides (NOx) in a system to purify exhaust discharged from an internal-combustion engine of an automobile, etc.

BACKGROUND ART

In an internal-combustion engine of an automobile, fossil fuel such as gasoline or gas oil is burnt. Exhaust that is generated along with the combustion includes, together with water and carbon dioxide, environmental pollutants such as unburned carbon monoxide (CO) and carbon hydride (HC), sulfur oxides (SOx), and nitrogen oxides (NOx). Recently, especially for environmental protection and to prevent living environment from being polluted, there are suggested various countermeasures to purify exhaust from an automobile.

As one countermeasure, there is known the use of an exhaust purification catalyst device. According to this device, three way catalyst for exhaust purification is arranged on the way of an exhaust system, where CO, HC, NOx and the like are decomposed by oxidation-reduction to be rendered harmless. In order to continuously keep decomposing NOx in the catalyst device, urea aqueous solution is sprayed to the catalyst from the upstream side of the catalyst device of the exhaust system. The urea aqueous solution has to have its concentration set to be in a specific urea concentration range so as to enhance the effect of decomposing NOx, and particularly a urea concentration of 32.5% is considered to be most desirable.

Urea solution, which is stored in a urea solution tank carried on an automobile, may have its concentration changed as time goes by, and furthermore, there may be raised unevenness in concentration distribution locally in the tank. Urea solution, which is to be supplied to a spray nozzle from the tank through a supply-pipe by means of a pump, is generally taken out from an outlet port located near the bottom of the tank. Thus, urea solution around the area has to be of a desired urea concentration so as to enhance the efficiency of the catalyst device.

On the other hand, conventionally, a urea concentration in urea solution is not directly measured. Furthermore, in an exhaust system, there is employed a method of arranging NOx sensors at the upstream side as well as at the downstream side of a catalyst device, and judging whether or not decomposition of NOx is suitably carried out based on the difference of NOx concentrations detected by these sensors. However, this method is employed to measure the effect of actual reduction of NOx, and cannot identify a urea concentration not only before spraying urea solution but also from the very beginning of spraying urea solution. Moreover, NOx sensors used in this method are not sufficient in sensitivity for realizing spraying urea solution of a desired concentration.

In Patent Document 1, there is disclosed a fluid identification method of making a heating element generate heat by applying current thereto, heating a temperature sensing element using thus generated heat, exerting a thermal influence on heat transfer from the heating element to the temperature sensing element by means of fluid to be identified, and determining the kind of the fluid to be identified based on an electric output corresponding to an electric resistance of the temperature sensing element, in which method current is applied to the heating element periodically.

However, since current is applied to the heating element periodically (with multiple pulses), this fluid identification method is required to take considerable time for identification, which makes it difficult to identify the fluid instantly. Furthermore, under this method, even if fluid identification can be carried out using a representative value for materials whose properties are significantly different from each other such as water, air, oil, it is difficult to identify a urea concentration correctly and promptly by applying this method to the above-described urea concentration identification for urea solution.

Patent Document 1: JP(A)-11-153561 (especially paragraphs [0042] to [0049])

DISCLOSURE OF THE INVENTION

Accordingly, the present invention has an object to overcome the above-mentioned drawbacks by providing an identification device for urea solution which can identify a urea concentration in urea solution correctly as well as promptly.

According to the present invention, there is provided a urea concentration identification device for identifying a urea concentration in urea solution stored in a tank, comprising a concentration identification sensor unit; and a support unit having one end to which the concentration identification sensor unit is attached and the other end provided with a mounting unit to be attached to an opening of the tank, wherein the concentration identification sensor unit includes an indirectly-heated concentration detector having a heating element and a temperature sensing element, and a liquid temperature detector for measuring the temperature of urea solution; the indirectly-heated concentration detector has a heat transfer member for concentration detector for exchanging heat with the urea solution; the liquid temperature detector has a heat transfer member for liquid temperature detector for exchanging heat with the urea solution; and a cover member is attached to the concentration identification sensor unit so as to surround the heat transfer member for concentration detector and the heat transfer member for liquid temperature detector to form a urea solution induction passage with its both ends opened, and wherein a single-pulse voltage is applied to the heating element of the indirectly-heated concentration detector to make the heating element generate heat, and an identification operation unit identifies the urea concentration based on an output of a concentration detection circuit including the temperature sensing element of the indirectly-heated concentration detector and the liquid temperature detector.

According to an aspect of the present invention, the identification operation unit identifies the urea concentration using a concentration correspondence voltage value corresponding to the difference between the initial temperature and the peak temperature of the temperature sensing element when the heating element generates heat. According to an aspect of the present invention, as a voltage value corresponding to the initial temperature of the temperature sensing element, an average initial voltage value which is obtained by sampling the initial voltage before starting the application of the single-pulse voltage to the heating element by a predetermined number of times and calculating the average thereof is used, and as a voltage value corresponding to the peak temperature of the temperature sensing element, an average peak voltage value which is obtained by sampling the peak voltage before ending the application of the single-pulse voltage to the heating element by a predetermined number of times and calculating the average thereof is used, and as the concentration correspondence voltage value, the difference between the average peak voltage value and the average initial voltage value is used.

According to an aspect of the present invention, a liquid temperature correspondence output value corresponding to the liquid temperature of the urea solution is input from the liquid temperature detector to the identification operation unit, and the identification operation unit identifies the urea concentration, using calibration curves indicative of the relation between the liquid temperature and the concentration correspondence voltage value prepared for a plurality of reference urea solutions whose urea concentrations are different from each other and given in advance, based on the liquid temperature correspondence output value and the concentration correspondence voltage value obtained for urea solution to be identified.

According to an aspect of the present invention, the identification operation unit has a microcomputer. According to an aspect of the present invention, a circuit board constituting the concentration detection circuit is arranged on the other end of the support unit, and a wire runs inside the support unit to electrically connect the concentration identification sensor unit to the circuit board. According to an aspect of the present invention, the microcomputer is arranged on a circuit board.

According to the present invention, since a urea concentration is identified for urea solution stored in a tank, a concentration identification sensor unit is arranged inside the tank, and urea concentration identification with desirable precision can be stably performed without being affected by external environmental conditions.

Furthermore, according to the present invention, since a urea concentration is identified at an identification operation unit based on an output of a concentration detection circuit by applying a single-pulse voltage to a heating element of an indirectly-heated concentration detector to make the heating element generate heat, a urea concentration in urea solution can be identified correctly as well as promptly. Especially, if a urea concentration is identified using a concentration correspondence voltage value corresponding to the difference between the initial temperature and the peak temperature of a temperature sensing element when the heating element generates heat, and the difference between an average peak voltage value and an average initial voltage value is used as the concentration correspondence voltage value, correct as well as prompt identification can be performed stably.

Furthermore, according to the present invention, since a cover member surrounds a heat transfer member for concentration detector and a heat transfer member for liquid temperature detector to form a urea solution induction passage with its both ends opened, urea solution around the heat transfer members has difficulty in raising a forced flow based on a foreign factor, which can improve the precision of the above-described concentration identification.

BEST MODE FOR CARRYING OUT THE INVENTION

The present invention will further be described below concerning the best modes with reference to the accompanying drawings.

Figure 1:
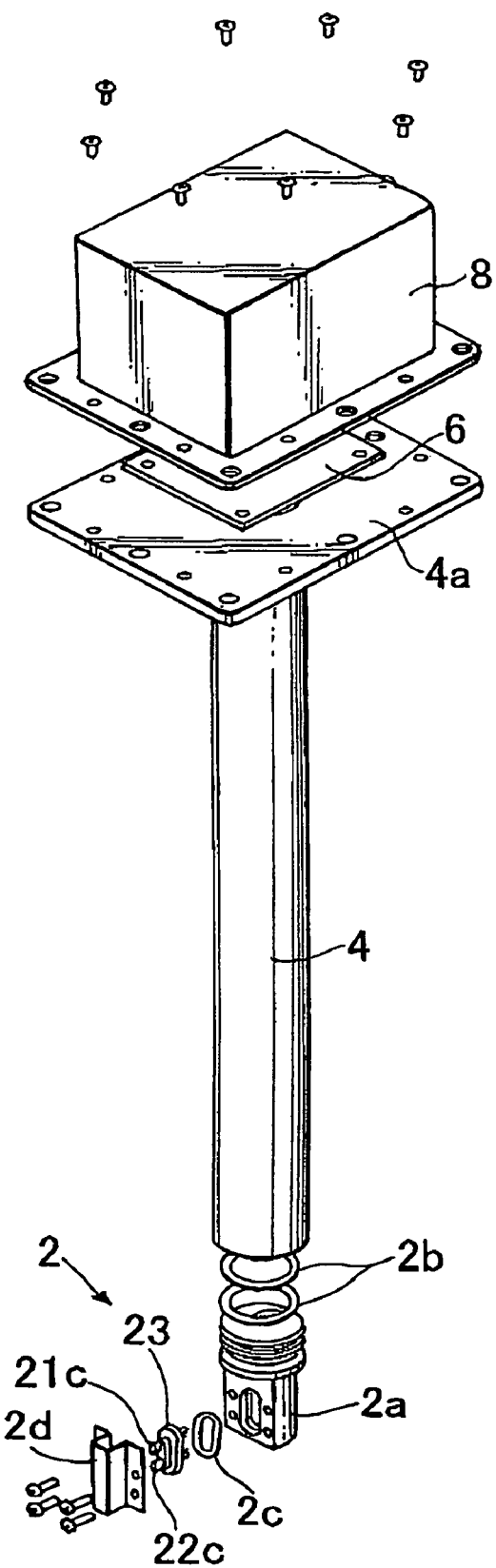
FIG. 1 shows an exploded perspective view of one embodiment of the urea concentration identification device according to the present invention.
Figure 2:
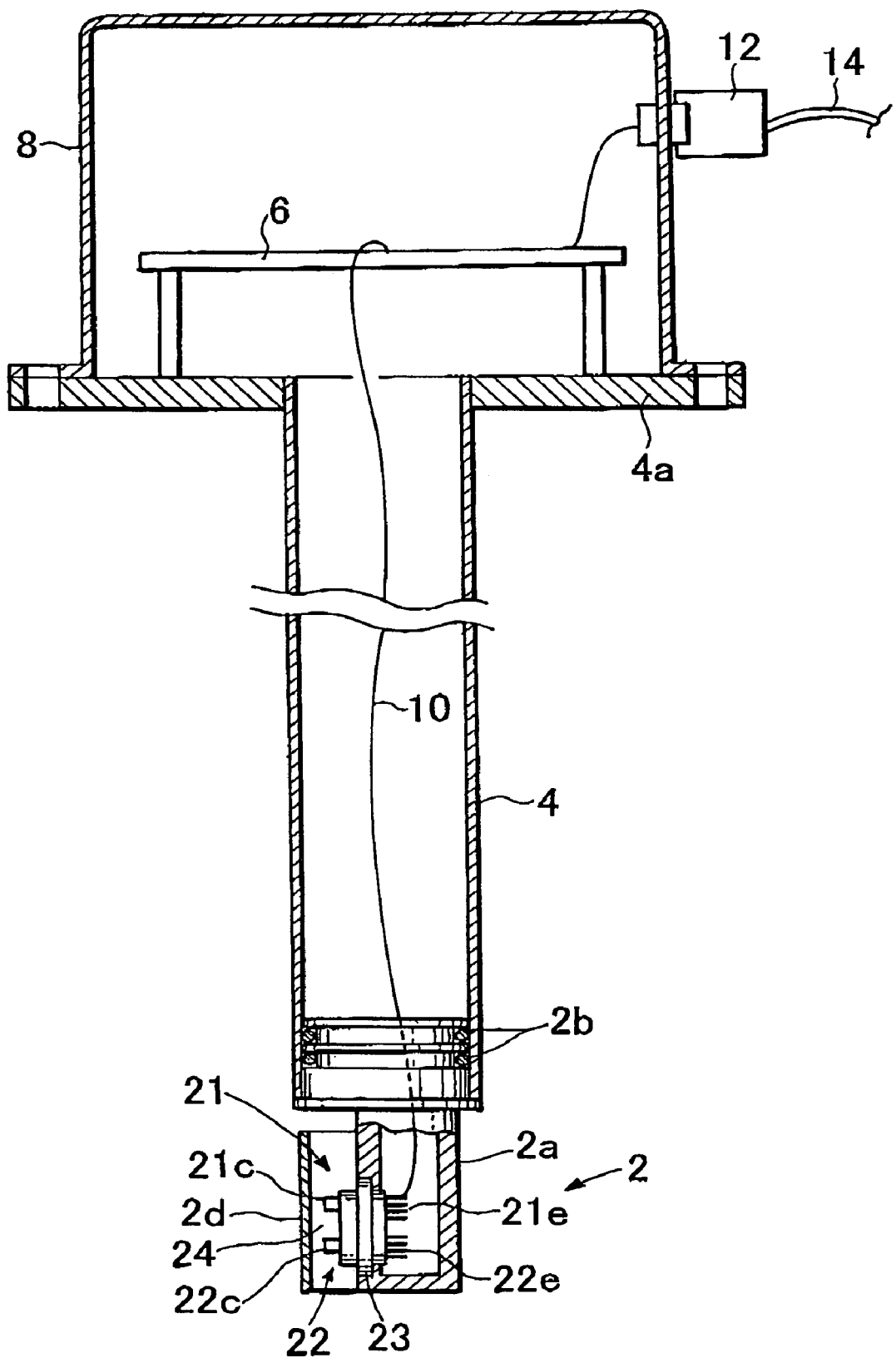
FIG. 2 shows a sectional view of the urea concentration identification device part of which is omitted.
Figure 3:
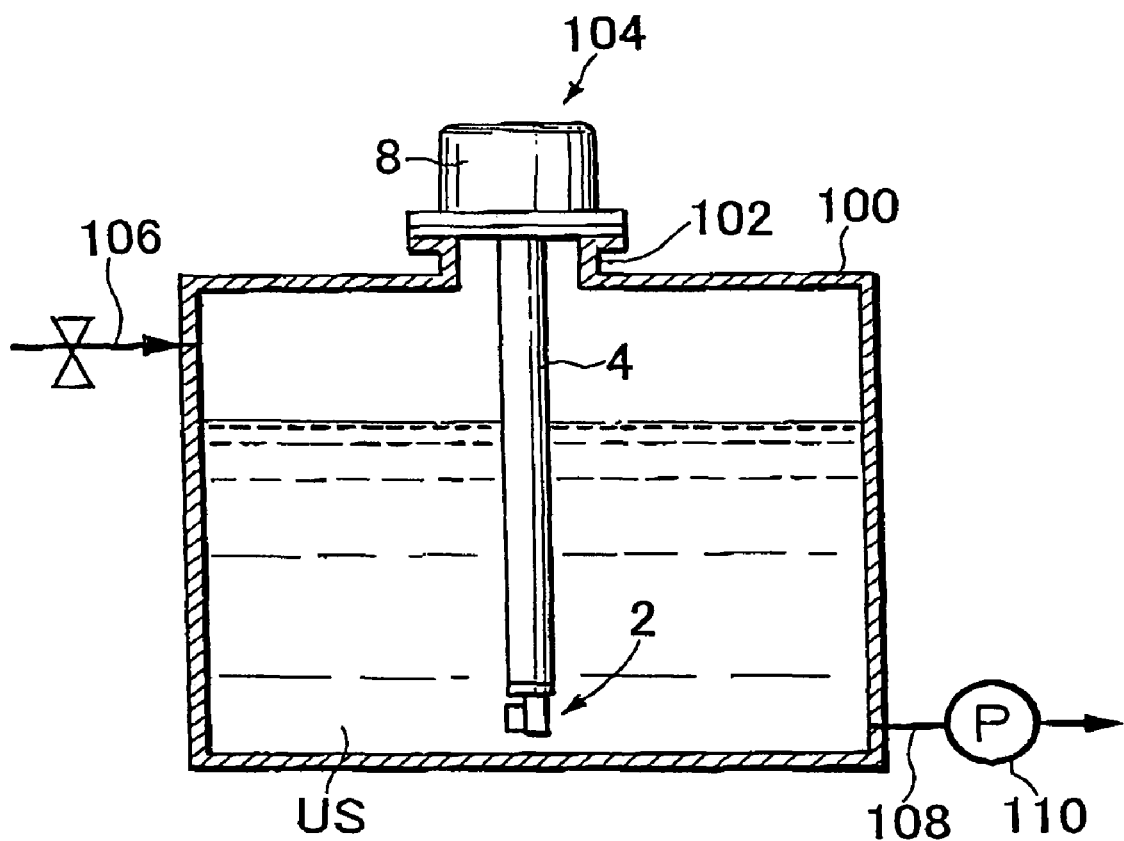
FIG. 3 shows a view indicative of the state of mounting the urea concentration identification device to a tank.

FIG. 1 shows an exploded perspective view of one embodiment of the urea concentration identification device according to the present invention, FIG. 2 shows a sectional view of the same, part of which is omitted, and FIG. 3 shows a view indicative of the state of mounting the same to a tank.

As shown in FIG. 3, a urea solution tank 100 for decomposing NOx, which constitutes an exhaust purification system carried on an automobile, etc., is provided with an opening 102 on the top thereof, and a urea concentration identification device 104 according to the present invention is mounted to the opening 102. To the tank 100, an inlet pipe 106 from which urea solution is let in and an outlet pipe 108 from which urea solution is taken out are fixed. The outlet pipe 108 is coupled to the tank 100 at a height located near the bottom thereof, and is coupled to a urea solution spray unit, not shown, through a urea solution supply pump 110. In an exhaust system, the urea solution spray unit arranged right before an exhaust purification catalyst device sprays urea solution to the catalyst device.

The urea concentration identification device 104 includes a concentration identification sensor unit 2 and a support unit 4. The concentration identification sensor unit 2 is attached to one end (bottom portion) of the support unit 4, and the other end (top portion) of the support unit 4 is provided with a mounting unit 4a to be attached to the opening 102 of the tank 100.

Figure 4:
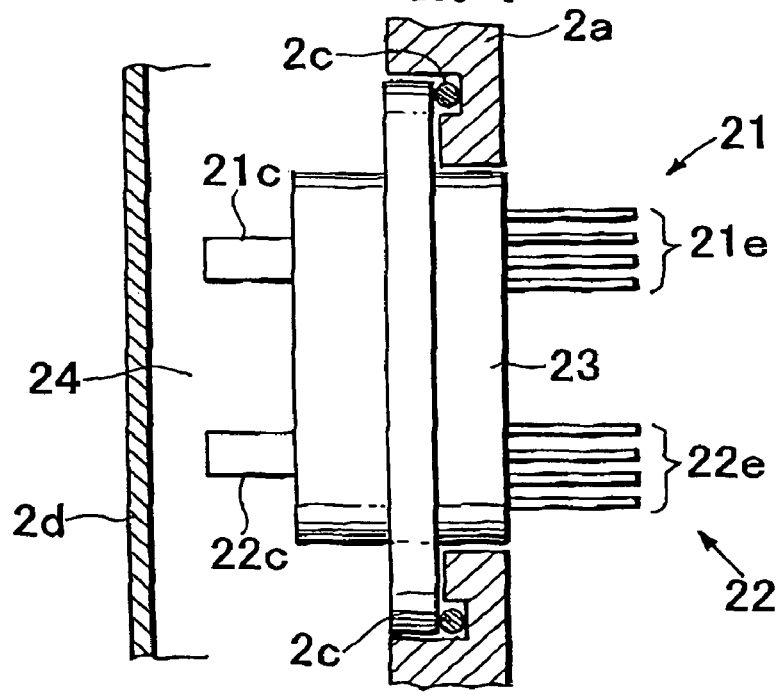
FIG. 4 shows an enlarged view of an indirectly-heated concentration detector and a liquid temperature detector.
Figure 5:
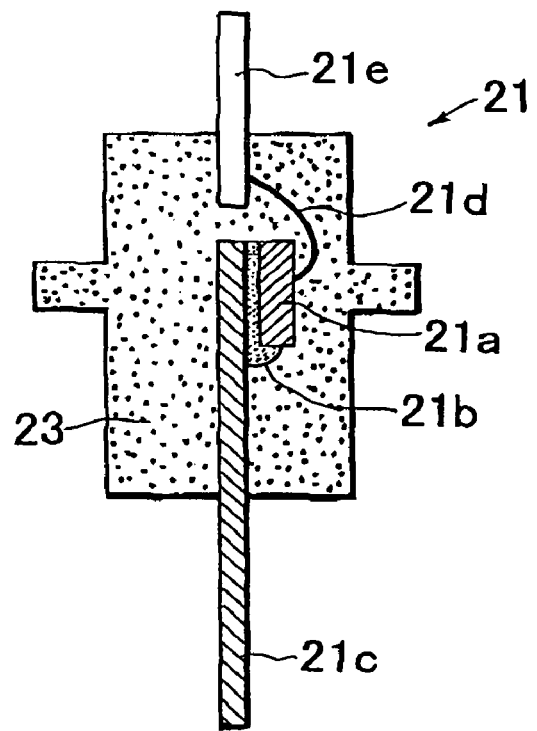
FIG. 5 shows a sectional view of the indirectly-heated concentration detector of FIG. 4.

The concentration identification sensor unit 2 includes an indirectly-heated concentration detector 21 that has a heating element and a temperature sensing element, and a liquid temperature detector 22 that measures the temperature of urea solution. The indirectly-heated concentration detector 21 and the liquid temperature detector 22 are arranged in the up and down direction with a predetermined distance situated therebetween. FIG. 4 shows an enlarged view of the indirectly-heated concentration detector 21 and the liquid temperature detector 22, and FIG. 5 shows a sectional view of the same.

As shown in those figures, the indirectly-heated concentration detector 21 and the liquid temperature detector 22 are united by a mold resin 23. As shown in FIG. 5, the indirectly-heated concentration detector 21 includes a thin film chip 21a having a heating element and a temperature sensing element, a metal fin 21c working as a heat transfer member for concentration detector which is coupled to the thin film chip 21a through a jointing material 21b, and external electrode terminals 21e which are electrically connected to an electrode of the heating element and an electrode of the temperature sensing element of the thin film chip 21a through a bonding wire 21d. The liquid temperature detector 22 has similar structure, and includes a metal fin 22c working as a heat transfer member for liquid temperature detector and external electrode terminals 22e.

Figure 6:
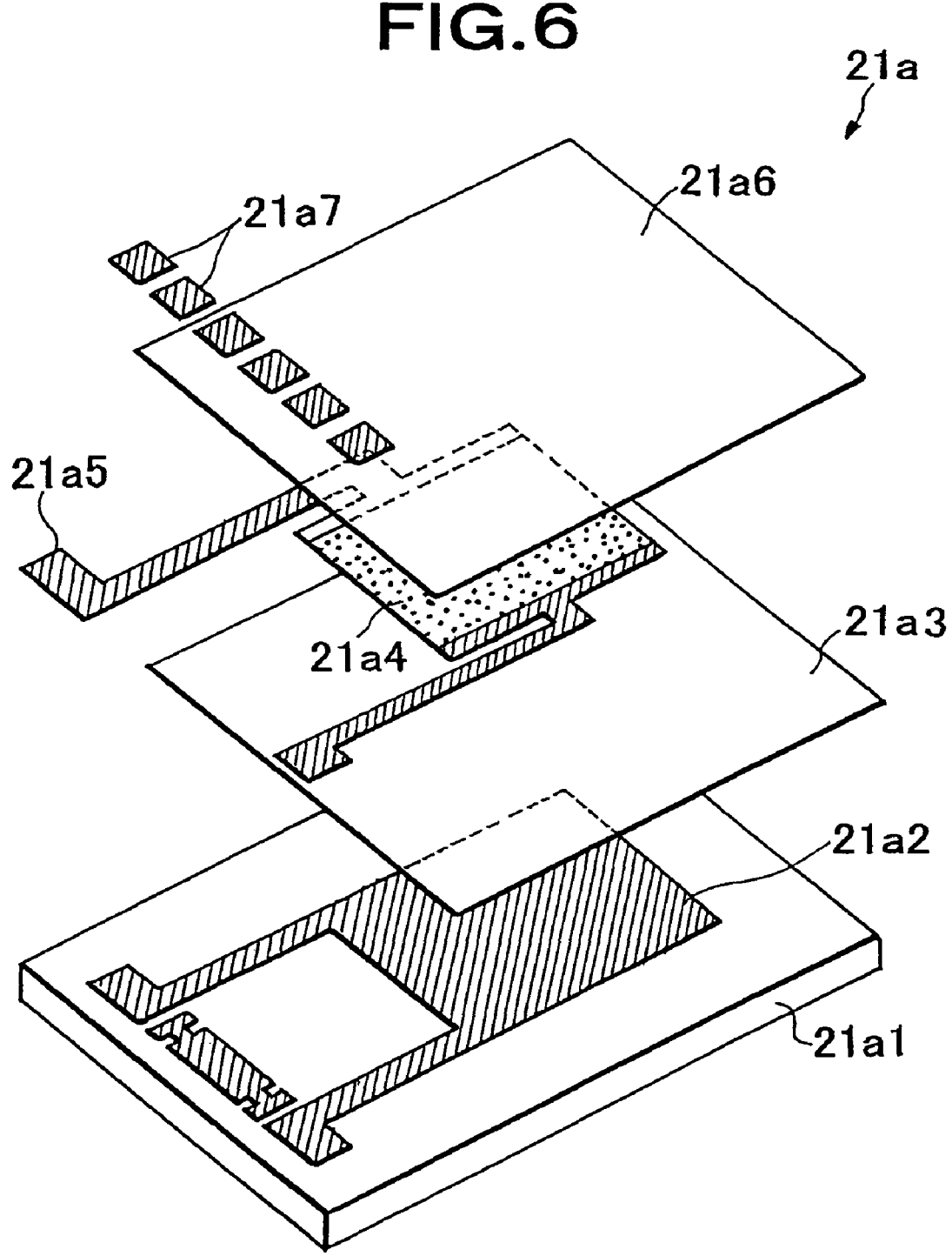
FIG. 6 shows an exploded perspective view of a thin film chip of the indirectly-heated concentration detector.

FIG. 6 shows an exploded perspective view of the thin film chip 21a of the indirectly-heated concentration detector 21. For example, the thin film chip 21a has a basal plate 21a1 made of $Al_2O_3$, a temperature sensing element 21a2 made of Pt, an inter-layer insulating film 21a3 made of $SiO_2$, a heating element 21a4 made of $TaSiO_2$ and a heating element electrode 21a5 made of Ni, a protective film 21a6 made of $SiO_2$, and electrode pads 21a7 made of Ti/Au, which are layered in this order. The temperature sensing element 21a2 is formed into a meandering pattern, which is not shown. The liquid temperature detector 22 has a thin film chip 22a of similar structure, and does not make a heating element work but makes only a temperature sensing element 22a2 work.

As shown in FIG. 1 and FIG. 2, the concentration identification sensor unit 2 has a basal body 2a mounted to the bottom end portion of the support unit 4, and O-rings 2b are used when mounting the basal body 2a. To the side of the basal body 2a, the mold resin 23 uniting the indirectly-heated concentration detector 21 and the liquid temperature detector 22 is attached through an O-ring 2c. To the basal body 2a, a cover member 2d is so attached as to surround the fin 21c for concentration detector and the fin 22c for liquid temperature detector. The cover member 2d forms a urea solution induction passage 24 that extends in the up and down direction, passing through the fin 21c for concentration detector and the fin 22c for liquid temperature detector sequentially, with its both upper and lower ends opened. Since the heat transfer membercover member 2d is attached to the basal body 2a, a flange portion of the mold resin 23 is pressed toward the basal body 2a, which fixes the mold resin 23 to the basal body 2a.

On the top portion of the support unit 4, a circuit board 6 constituting a concentration detection circuit to be described later is arranged, and a circuit board cover member 8 is so mounted as to cover the circuit board 6. As shown in FIG. 2, inside the support unit 4, a wire 10 runs to electrically connect the indirectly-heated concentration detector 21 and liquid temperature detector 22 of the concentration identification sensor unit 2 to the circuit board 6. The circuit board 6 has a microcomputer arranged thereon that works as an identification operation unit to be described later. Through a connector 12 attached to the circuit board cover member 8, a wire 14 is provided for carrying out communication between the circuit board 6 and the outside. The identification operation unit may be arranged not on the circuit board 6 but outside the circuit board cover member 8, in which case the circuit board 6 and the identification operation unit are connected through the wire 14.

The basal body 2a and heat transfer membercover member 2d of the concentration identification sensor unit 2, support unit 4, and circuit board cover member 8 are made of corrosion-proof material such as stainless steel.

Figure 7:
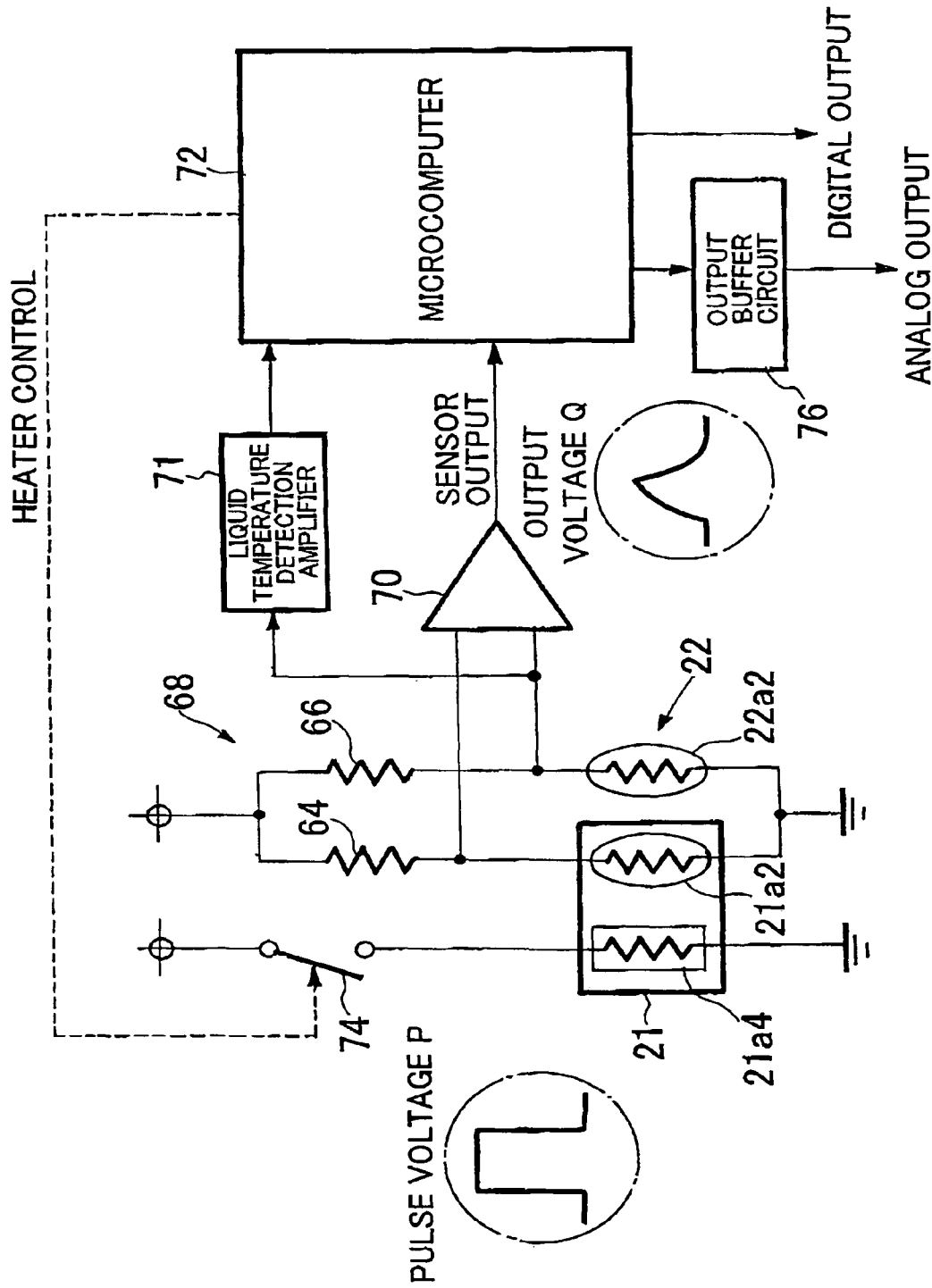
FIG. 7 shows a block diagram of a circuit for identifying a concentration.

FIG. 7 shows a block diagram for identifying a concentration in the present embodiment. The temperature sensing element 21a2 of the indirectly-heated concentration detector 21, the temperature sensing element 22a2 of the liquid temperature detector 22, and two resistors 64, 66 form a bridge circuit 68. An output of the bridge circuit 68 is input to a differential amplifier 70, and an output of the differential amplifier (also referred to as concentration detection circuit output or sensor output) is input to a microcomputer 72 that works as an identification operation unit through an A/D converter, not shown. Also, the microcomputer 72 receives a liquid temperature correspondence output value corresponding to the liquid temperature of urea solution from the temperature sensing element 22a2 of the liquid temperature detector 22 through a liquid temperature detection amplifier 71. On the other hand, the microcomputer 72 outputs a heater control signal to a switch 74 located on an electric pathway to the heating element 21a4 of the indirectly-heated concentration detector 21 to control the opening and closing of the switch.

Next, the performance of concentration identification in the embodiment will be explained.

When urea solution US is stored in the tank 100, the urea solution induction passage 24 formed by the heat transfer membercover member 2d of the concentration identification sensor unit 2 is filled with the urea solution US. The urea solution US not only in the urea solution induction passage 24 but also in the entire tank 100 substantially does not flow.

When the microcomputer 72 sends the heater control signal to the switch 74 to close the switch 74 for a predetermined period of time (for example, four seconds), a single-pulse voltage P of a predetermined height (for example, 10V) is applied to the heating element 21a4 to make the heating element generate heat. At this time, as shown in FIG. 8, an output voltage (sensor output) Q of the differential amplifier 70 gradually increases when the voltage P is being applied to the heating element 21a4, and gradually decreases after the application of the voltage P to the heating element 21a4 is ended.

Figure 8:
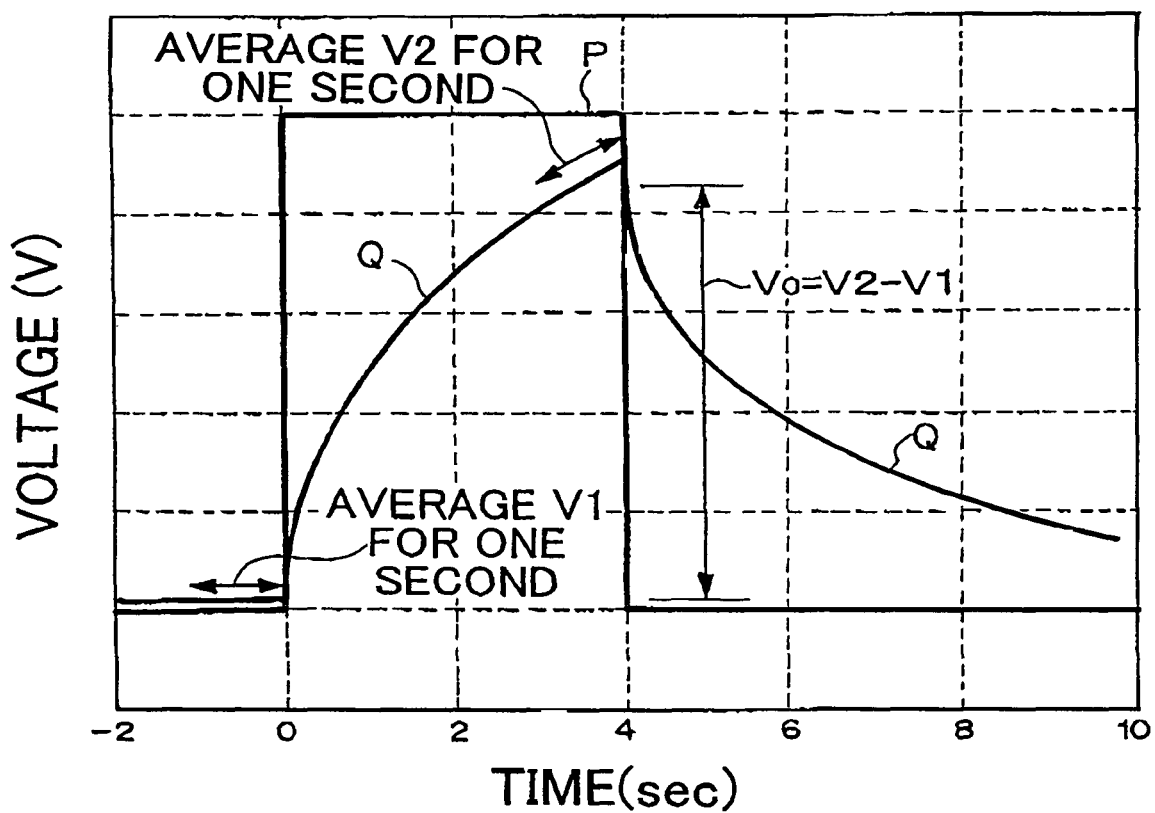
FIG. 8 shows a view indicative of the relation between a single-pulse voltage P applied to a heating element and a sensor output Q.

As shown in FIG. 8, the microcomputer 72 samples the sensor output by a predetermined number of times (for example, 256 times) for a predetermined time period (for example, for one second) before starting the application of voltage P to the heating element 21a4, and obtains an average initial voltage value V1 by carrying out an operation to obtain the average value thereof. The average initial voltage value V1 corresponds to the initial temperature of the temperature sensing element 21a2. Furthermore, as shown in FIG. 8, the microcomputer 72 samples the sensor output by a predetermined number of times (for example, 256 times) for a predetermined time period (for example, for one second) before ending the application of voltage P to the heating element 21a4, and obtains an average peak voltage value V2 by carrying out an operation to obtain the average value thereof. The average peak voltage value V2 corresponds to the peak temperature of the temperature sensing element 21a2. Then, the difference between the average initial voltage value V1 and the average peak voltage value V2 (=V2–V1) is obtained as a concentration correspondence voltage value V0.

Figure 9:
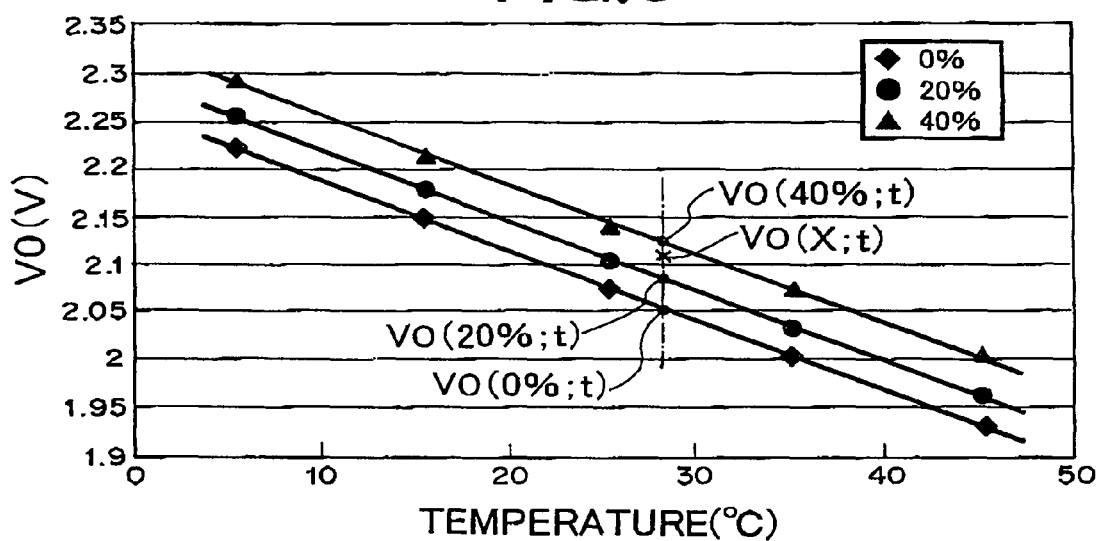
FIG. 9 shows an example of calibration curves.

On the other hand, in the above-described method, calibration curves indicative of the relation between the temperature and the concentration correspondence voltage value V0 are obtained in advance with respect to several urea aqueous solutions (reference urea solutions) whose urea concentrations are given in advance, and thus obtained calibration curves are stored in a storage means of the microcomputer 72. FIG. 9 shows an example of the calibration curves. In this example, calibration curves are prepared for reference urea solutions whose urea concentrations are 0%, 20%, and 40%.

Figure 10:
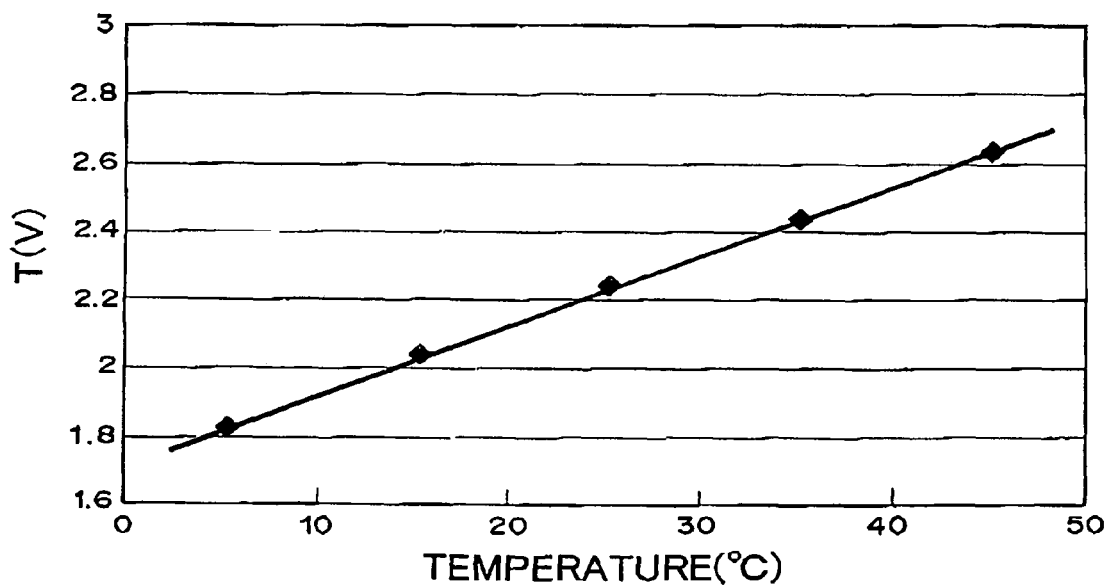
FIG. 10 shows an example of a liquid temperature correspondence output value T.
Figure 11:
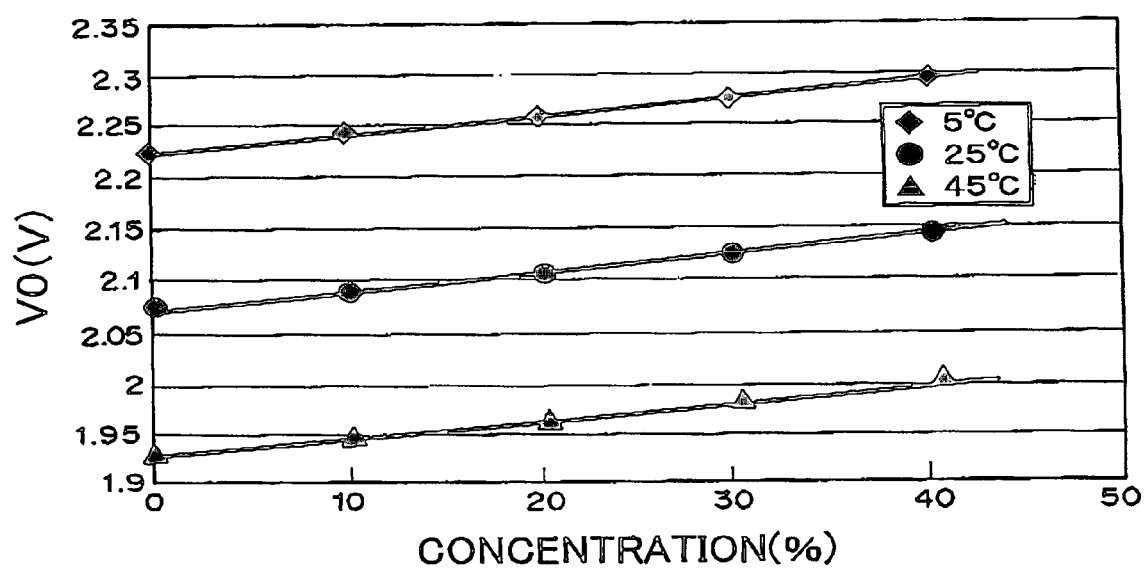
FIG. 11 shows an example of the relation between a concentration correspondence voltage value V0 and an actual concentration.

As shown in FIG. 9, since the concentration correspondence voltage value V0 depends on the temperature, when measuring a concentration of urea solution to be measured using the calibration curves, a liquid temperature correspondence output value T that is input from the temperature sensing element 22a2 of the liquid temperature detector 22 through the liquid temperature detection amplifier 71 is also used. FIG. 10 shows an example of the liquid temperature correspondence output value T. Such a calibration curve is also stored in the storage means of the microcomputer 72. Furthermore, FIG. 11 shows an example of the relation between the concentration correspondence voltage value V0 and an actual concentration obtained from urea solutions whose temperatures and urea concentrations are different from each other.

From the liquid temperature correspondence output value T obtained for urea solution to be measured, a temperature value "t" is obtained using the calibration curve shown in FIG. 10. Then, concentration correspondence voltage values V0 (0% ; t), V0 (20% ; t), and V0 (40% ; t) corresponding to the temperature value "t" are obtained on the respective calibration curves shown in FIG. 9. Then, it is determined how much percentage of urea concentration corresponds to the concentration correspondence voltage value V0 (X ; t) obtained for urea solution to be measured, by carrying out proportion operation using at least two of the concentration correspondence voltage values V0 (0% ; t), V0 (20% ; t), and V0 (40% ; t), for example, V0 (20% ; t) and V0 (40% ; t), on the respective calibration curves. As described above, identification of a urea concentration can be carried out correctly as well as promptly (instantly). On the other hand, as the calibration curves shown in FIG. 9, those using the liquid temperature correspondence output value T instead of the temperature can be employed, which can omit storing the calibration curve shown in FIG. 10.

Figure 12:
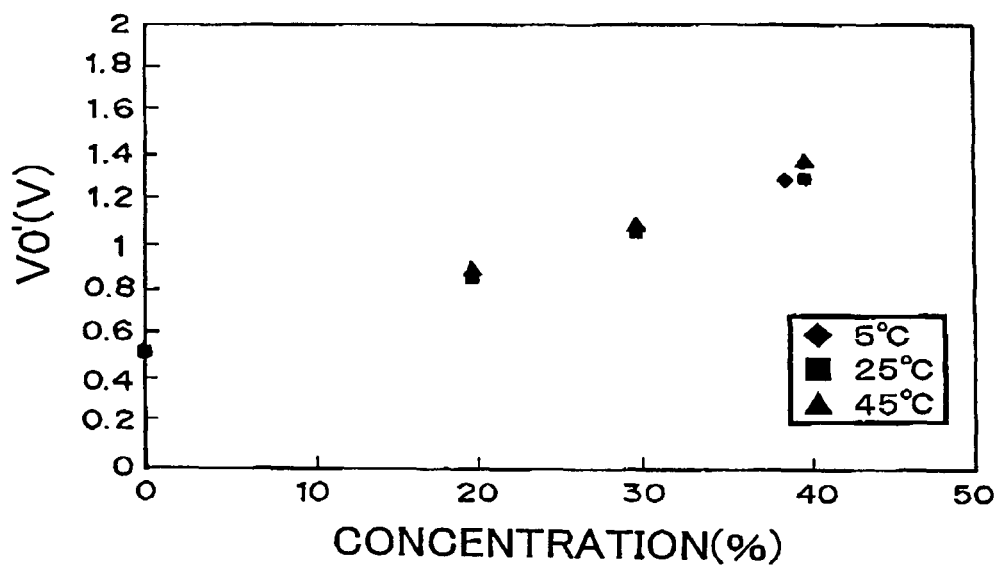
FIG. 12 shows an example of the relation between a concentration correspondence analog output voltage value V0' and an actual concentration.
Figure 13:
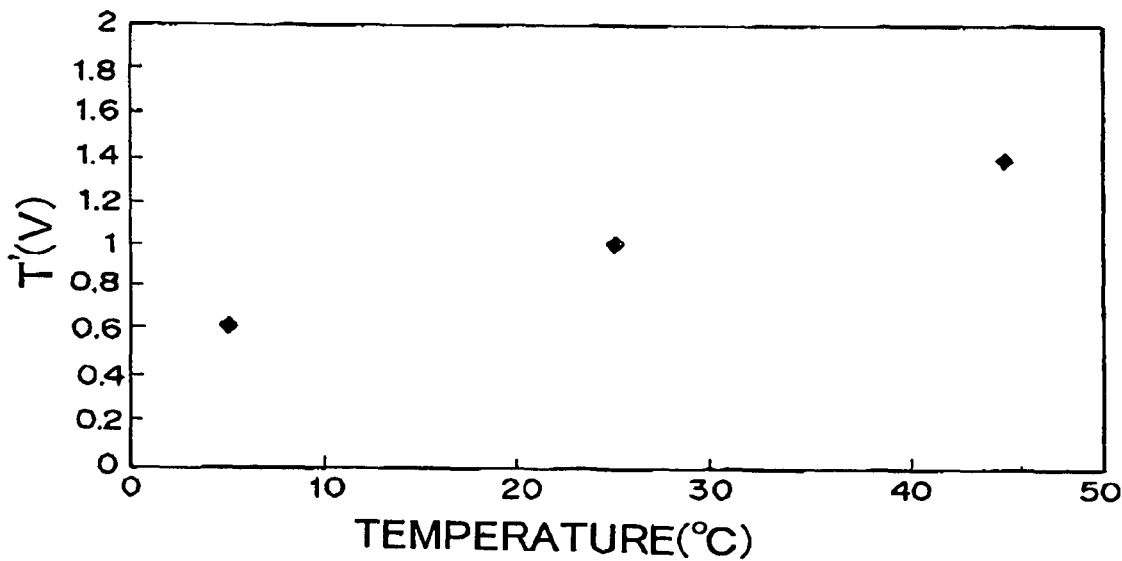
FIG. 13 shows an example of the relation between a liquid temperature correspondence analog output voltage value T' and an actual temperature, wherein reference numeral 2 denotes a concentration identification sensor unit, 2a basal body, 2b, 2c O-ring, 2d heat transfer membercover member, 21 indirectly-heated concentration detector, 22 liquid temperature detector, 23 mold resin, 24 urea solution induction passage, 21a thin film chip, 21b jointing material, 21c, 22c metal fin, 21d bonding wire, 21e, 22e external electrode terminal, 21a1 basal plate, 21a2, 22a2 temperature sensing element, 21a3 inter-layer insulating film, 21a4 heating element, 21a5 heating element electrode, 21a6 protective film, 21a7 electrode pad, 4 support unit, 6 circuit board, 8 circuit board cover member, 10,14 wire, 12 connector, 64, 66 resistor, 68 bridge circuit, 70 differential amplifier, 71 liquid temperature detection amplifier, 72 microcomputer, 74 switch, 76 output buffer circuit, 100 urea solution tank, 102 opening, 104 urea concentration identification device, 106 inlet pipe, 108 outlet pipe, 110 urea solution supply pump, and US denotes a urea solution.

Then, a signal indicative of thus obtained concentration value is output to an output buffer circuit 76 shown in FIG. 7 through a D/A converter, not shown, and is then output to a main computer (ECU), not shown, for carrying out combustion control for an engine of an automobile as an analog output. FIG. 12 shows an example of the relation between an analog output voltage value V0' corresponding to a concentration and an actual concentration. The difference with respect to temperature in this relation is small, which enables practical use. Furthermore, FIG. 13 shows an example of the relation between an analog output voltage value T' corresponding to a liquid temperature and an actual temperature. The liquid temperature correspondence analog output voltage value T' is also output to the main computer (ECU). On the other hand, signals indicative of the concentration value and the liquid temperature value are taken out as digital outputs according to need, and are input to devices for displaying, alarming, and other performances.

The above-described urea concentration identification for urea solution is based on the principle that there is a correlation between a kinetic viscosity of urea solution under natural convection and a sensor output. In order to enhance the precision of concentration identification, it is desirable that urea solution around the fin 21c for concentration detector and fin 22c for liquid temperature detector has difficulty in raising a forced flow based on a foreign factor as much as possible. From such a viewpoint, it is desirable to use the heat transfer membercover member 2d, especially one having urea solution induction passage 24 extending in the up and down direction. The heat transfer membercover member 2d works also as a protection member that prevents a foreign matter from coming into contact therewith.

As described above, it is considered that the optimal concentration of urea solution to be used in an exhaust purification system is 32.5%. Accordingly, setting a range between 25% to 40% or 30% to 35% as an appropriate range, an alarm may be given in case an identification result deviating from the appropriate range is obtained. Furthermore, in case urea in the tank is reduced and the urea solution induction passage 24 comes to be unfilled with urea solution, a concentration correspondence voltage value of urea solution significantly deviating from the appropriate range is obtained in identifying a concentration, in which case a required alarm may also be given. Similarly, in case liquid (for example, salt solution, coolant water, etc.) whose correlation between a kinetic viscosity thereof and a sensor output is different from that of urea solution is poured into the tank by accident, a concentration correspondence voltage value different from that within the appropriate range which is obtained when using urea solution whose liquid temperature is equal to that of thus poured liquid is obtained in identifying a concentration, in which case a required alarm may also be given.

Furthermore, based on the liquid temperature correspondence output value T sent from the liquid temperature detector 22, in case it is detected that urea solution has its temperature reduced to a temperature around which urea solution is frozen (around –13° C.), an alarm may be given.

What is claimed is:

1. A urea concentration identification device for identifying a urea concentration in urea solution stored in a tank, comprising:
   a concentration identification sensor unit comprising a concentration detector having a heat transfer member and a liquid temperature detector having a heat transfer member; and
   a support unit having one end to which the concentration identification sensor unit is attached and the other end provided with a mounting unit to be attached to an opening of the tank;
   wherein a heat transfer member cover member is provided so as to surround the heat transfer member of the concentration detector and the heat transfer member of the liquid temperature detector, the heat transfer member cover member forming a passage with open ends to allow urea solution to pass through the heat transfer member of the concentration detector and the heat transfer member of the liquid temperature detector.

2. The urea concentration identification device for the urea solution as claimed in claim 1, wherein the concentration detector has a plate shape.

3. The urea concentration identification device for the urea solution as claimed in claim 1, wherein the liquid temperature detector has a plane or membrane shape.

4. The urea concentration identification device for the urea solution as claimed in claim 1, wherein the concentration detector has a plane or membrane shape.

5. The urea concentration identification device for the urea solution as claimed in claim 1, wherein the concentration detector and the liquid temperature detector are arranged on the same level.

* * * * *